(12) United States Patent
Lin et al.

(10) Patent No.: US 12,076,435 B2
(45) Date of Patent: Sep. 3, 2024

(54) **METHOD FOR SKIN BRIGHTENING USING *CHENOPODIUM FORMOSANUM* (DJULIS) EXTRACT**

(71) Applicant: TCI CO., LTD., Taipei (TW)

(72) Inventors: Yung-Hsiang Lin, Taipei (TW); Zih-Yi Li, Taipei (TW)

(73) Assignee: TCI CO., LTD., Taipei (TW)

( * ) Notice: Subject to any disclaimer, the term of this patent is extended or adjusted under 35 U.S.C. 154(b) by 13 days.

(21) Appl. No.: 18/063,694

(22) Filed: Dec. 9, 2022

(65) Prior Publication Data

US 2023/0240974 A1     Aug. 3, 2023

Related U.S. Application Data

(63) Continuation of application No. 17/095,763, filed on Nov. 12, 2020, now abandoned.

(60) Provisional application No. 62/934,014, filed on Nov. 12, 2019.

(51) Int. Cl.
| | | |
|---|---|---|
| *A61K 36/00* | (2006.01) | |
| *A61K 8/9789* | (2017.01) | |
| *A61Q 19/00* | (2006.01) | |
| *A61Q 19/02* | (2006.01) | |
| *A61Q 19/08* | (2006.01) | |

(52) U.S. Cl.
CPC .......... *A61K 8/9789* (2017.08); *A61Q 19/007* (2013.01); *A61Q 19/02* (2013.01); *A61Q 19/08* (2013.01)

(58) Field of Classification Search
None
See application file for complete search history.

(56) References Cited

U.S. PATENT DOCUMENTS

2015/0265527 A1* 9/2015 Su .......................... A61Q 19/08
424/725

FOREIGN PATENT DOCUMENTS

TW         201900150 A       1/2019

OTHER PUBLICATIONS

Boo et al. (2019) Antioxidants 8, 332 (18 pages) (Year: 2019).*
Graf et al. (2014) International Journal of Cosmetic Science 37, 212-221. (Year: 2014).*
Chen et al. (2019) Food Bioscience 32: 100469 (11 pages) (Year: 2019).*
Chuang et al. (2018) Int. J. Mol. Sci. 19, 2726 (12 pages) (Year: 2018).*
Escribano et al. (2017) Food Chemistry 234: 285-294. (Year: 2017).*
Raskin et al. (2004) Current Pharmaceutical Design, 10, 3419-3429. (Year: 2004).*
Revilla et al. (1998) J. Agric. Food Chem. 46, 4592-4597. (Year: 1998).*
Sohretoglu et al. (2018) Bioorganic Chemistry 81: 168-174. (Year: 2018).*
Zuo et al. (2018) Chin. Med. 13:51 (12 pages). (Year: 2018).*
Evaluation of the effects of Red Quinoa Extract and fermentation broth on skin whitening and moisturizing, Ping-Hsin Huang et al., Cardinal Tien Junior College of Healthcare and Management, No. 15, Dec. 2017, pp. 24-30 especially for the right column of p. 25, the left column of p. 27, and the left column of p. 28.
The "skin" secret of "Chenopodium formosanum" food—Explore the antioxidant effect of Chenopodium formosanum, Juan-Xiang Su, The 58th Primary & Secondary School Science Fair of the Republic of China, Jul. 23, 2018 to Jul. 27, 2018, especially for p. 7, table 4-2-1-1-3-1 of p. 13.

* cited by examiner

*Primary Examiner* — Russell G Fiebig
(74) *Attorney, Agent, or Firm* — Chich-Mei Wang

(57) ABSTRACT

A method for skin brightening using a *Chenopodium formosanum* (Djulis) extract. In particular, the *Chenopodium formosanum* (Djulis) extract is obtained with an aqueous solvent.

7 Claims, 6 Drawing Sheets

Specification includes a Sequence Listing.

METHOD FOR SKIN BRIGHTENING USING *CHENOPODIUM FORMOSANUM* (*DJULIS*) EXTRACT

CROSS-REFERENCE TO RELATED APPLICATION

This application is a continuation of U.S. patent application Ser. No. 17/095,763 filed on Nov. 12, 2020, which claims the benefit of U.S. provisional application No. 62/934,014, filed on Nov. 12, 2019, the entirety of which are incorporated herein by reference.

REFERENCE OF AN ELECTRONIC SEQUENCE LISTING

The contents of the electronic sequence listing (2138—US-UT002-CON_SEQLIST_ST26.xml; Size: 11 KB; and Date of Creation: Mar. 3, 2023) is incorporated herein by reference in its entirety.

BACKGROUND

Technical Field

The present invention relates to a use of *Chenopodium formosanum* (Djulis) extract, particulary to the use of *Chenopodium formosanum* (Djulis) extract for the use of antioxidation and improving skin appearance, including skin moisturizing, skin whitening, and skin wrinkle smoothing.

Related Art

*Chenopodium formosanum* (Djulis), also known as Taiwan quinoa, red quinoa, purple quinoa, and rainbow rice, is an annual herb and an endemic species found in Taiwan. It is a close relative of quinoa and belongs to the Chenopodiaceae family and the genus *Chenopodium*. Distributed in the middle and low altitude mountain areas of central and southern Taiwan, it has more than a hundred years in aboriginal farming history. At present, the aboriginal tribe of Paiwan in Eastern Taiwan has the most abundant seed resources. Red quinoa is edible, and its seedlings, tender stems, and flower spikes can be added to cooking or boiling soup. Red quinoa seeds can also be ground into a powder to serve as raw materials for glutinous rice balls.

The protein content of red quinoa is twice that of rice. The fruit of red quinoa is often dried, hulled, and mixed with other grains to serve as general edible rice. In food processing, different processing methods (steaming, microwave, roasting, frying, and puffing) can be used to make rice balls, biscuits, potato balls, puffs, mochi, muffins, and fragrant rice products. Red quinoa can serve as a garnish for plating and provide rich nutritional value, and is gradually being loved by more and more consumers.

SUMMARY

The present invention discloses a red quinoa extract for improving skin conditions. The composition can be used as an antioxidant or for skin whitening and skin moisturizing purposes.

In some embodiments, the red quinoa extract scavenges free radicals in cells, wherein the red quinoa extract is extracted with an aqueous solvent. In some embodiments, the cell is a skin cell.

In some embodiments, the red quinoa extract achieves the antioxidant effect by enhancing the expression level of antioxidant-related genes.

In some embodiments, the antioxidant-related genes include at least one of the SOD1 gene, the SOD2 gene, or the CAT gene.

In some embodiments, the red quinoa extract achieves the antioxidant effect by increasing the abundance of antioxidant enzymes in a body.

In some embodiments, the Degrees Brix value of the red quinoa extract is 7.0±5.

In some embodiments, the red quinoa extract is used to prepare a composition for improving skin condition, wherein the red quinoa extract is extracted with an aqueous solvent.

In some embodiments, the red quinoa extract is used to prepare a skin whitening composition, wherein the red quinoa extract is extracted with an aqueous solvent.

In some embodiments, the red quinoa extract achieves the skin whitening effect by inhibiting tyrosinase activity and/or reducing the amount of melanin production.

In some embodiments, the red quinoa extract is used to prepare a skin moisturizing composition, and the red quinoa extract is extracted with an aqueous solvent.

In some embodiments, the red quinoa extract achieves the skin's moisturizing effect by enhancing the expression of skin moisturizing-related genes.

In some embodiments, skin moisturizing-related genes include at least one of the TGM1 gene, the KRT1 gene, the KRT10 gene, and the KRT14 gene.

In some embodiments, the aqueous solvent is water or a solvent containing organic acids. In some embodiments, the concentration of the organic acid is 0.05%-1.00%.

In some embodiments, the red quinoa extract is formed by first extracting red quinoa with an aqueous solvent and then undergoing glycolysis using a saccharification enzyme.

In summary, the red quinoa extract of any embodiment can be used to prepare an antioxidant composition. The red quinoa extract of any embodiment can be used to prepare a composition that improves the expression of antioxidant-related genes (such as the SOD1 gene, the SOD2 gene, or the CAT gene) in cells. The red quinoa extract of any embodiment can be used to prepare a composition for enhancing antioxidant enzymes in the body. The red quinoa extract of any embodiment can be used to prepare a skin moisturizing composition. The red quinoa extract of any embodiment can be used to prepare a composition that improves the expression of moisturizing-related genes (such as the TGM1 gene, the KRT1 gene, the KRT10 gene, the KRT14 gene) in cells. The red quinoa extract of any embodiment can be used to prepare a skin whitening composition. The red quinoa extract of any embodiment can be used to prepare a composition that inhibits tyrosine expression. The red quinoa extract of any embodiment can be used to prepare a composition that inhibits melanin formation.

DETAILED DESCRIPTION

Some embodiments of the present invention are described below. The present invention can be practiced in many different embodiments. It should be noted that the scope of the present invention is not limited to the embodiments specified in the present specification.

Microsoft's Excel software is used for statistical analysis in the present invention. The data are expressed as mean±standard deviation (SD), and the differences between groups are analyzed by student's t-test. In the diagram, "*" represents a p-value smaller than 0.05, "" represents a p-value smaller than 0.01, and "*" represents a p-value smaller than 0.001. The more "*"s are present, the more significant is the statistical difference.

The numerical values used in this article are approximate, and all experimental data all include a margin of error of 10%. In some embodiments, the margin of error is 5%.

In this article, "wt %" refers to percentage by weight, and "vol %" refers to percentage by volume.

As used herein, the term "extract" refers to a product prepared through extraction. The extract can be presented in the form of a liquid solution or a form of a concentrate or essence containing no or little solvent.

As used herein, "raw red quinoa material" generally refers to the plant's seeds, wherein the seeds may include fresh red quinoa, dried red quinoa, or red quinoa processed by other physical methods. The physical methods may include chopping, dicing, or crushing. Any physical process that renders the seed different from its original physical property is considered a physical method.

Figure 1:
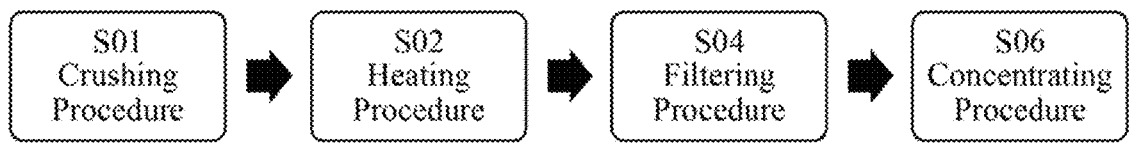
FIG. 1 shows an embodiment of a method for preparing red quinoa extract.

Referring to FIG. 1, in some embodiments, the red quinoa extract is extracted from raw red quinoa material with an aqueous solvent. In some embodiments, the red quinoa (*Chenopodium formosanum* (Djulis)) extract is obtained by sequentially performing the crushing procedure S01, heating procedure S02, filtering procedure S04, and concentrating procedure S06.

In some embodiments, the raw red quinoa material is hulled red quinoa seeds. In some embodiments, the red quinoa raw material may be fresh or dried red quinoa seeds.

In some embodiments, the crushing procedure S01 refers to grinding or crushing the raw red quinoa material until it becomes powdered raw red quinoa material. A juicer, a blender, or a homogenizer can be used to perform the crushing procedure 01.

In some embodiments, the heating procedure S02 refers to mixing powdered raw red quinoa material with an aqueous solvent and heating it for a fixed period. In some embodiments, heating refers to increasing the raw red quinoa material's temperature and its aqueous solvent to 50° C. to 100° C. In some embodiments, a fixed period of time refers to 0.5 hours to 3 hours. An example of an embodiment is mixing the powdered raw red quinoa material with an aqueous solvent and increasing the temperature of the solution to 85° C. and maintaining such temperature for 1 hour.

In some embodiments, during the heating procedure S02, the weight ratio of the aqueous solvent to the raw red quinoa material ranges from is 5:1-20:1. For example, the weight ratio of the aqueous solvent to the raw red quinoa material can be 10:1.

In some embodiments, the aqueous solvent is water or a water solvent containing organic acids. In some embodiments, the concentration of the organic acid is 0.05% to 1.00%. In some embodiments, the organic acid and its concentration are at an edible state. In some embodiments, the organic acid may be citric acid, malic acid, tartaric acid, lactic acid, gluconic acid, acetic acid, but is not limited thereto.

An example of an embodiment is mixing 90 kg of raw red quinoa material with 900 kg of water and 0.63 kg of citric acid, heating them to 100° C., and maintaining them at 100° C. for 0.5 hours. Another example is mixing 90 kg of raw red quinoa material with 900 kg of water and 0.7 kg of citric acid and then heating them to 85° C. and maintaining 85° C. for 1 hour.

In some embodiments, the filtering procedure S04 refers to passing the heated (or cooled) raw red quinoa material and the aqueous solvent through a filter to filter out the solids or large particles in the solvent to form a filtrate. In some embodiments, the filter is a 400-mesh filter.

Figure 2:
FIG. 2 shows another embodiment of a method for preparing red quinoa extract.

Referring to FIG. 2, in some embodiments, between the heating procedure 02 and the filtering procedure S04 is a cooling process S03. The cooling process S03 refers to cooling the processed raw red quinoa materials and its aqueous solvent to room temperature.

In some embodiments, the concentrating procedure S06 refers to obtaining a first filtrate by concentrating the filtrate obtained from the filtering procedure S04 under reduced pressure (brand/model: BUCHI-Rotavapor R-100). In some embodiments, the first extract is the red quinoa extract. In some embodiments, the concentrating procedure S06 provides an environment of 40° C.-70° C. with reduced atmospheric pressure for concentrating. An example of an embodiment of the red quinoa extract is obtained by first crushing raw red quinoa material into powder through the crushing procedure S01, then undergoing the heating procedure S02, the filtering procedure, and the concentrating procedures S06.

In some embodiments, between the filtering procedure S04 and the concentrating procedure S06 is a glycolyzing procedure S05. During the glycolyzing procedure S05, a glycolysis enzyme is added to, stirred with, and mixed with the filtrate obtained from the filtering procedure S04 and then allowed to stand for at least 1 hour to give a glycolyzed solution. Glycolysis enzymes further enhance the effect of bioactive ingredients in the red quinoa extract. In some embodiments, the glycolysis enzymes may be α-amylase, [beta]-amylase, glucoamylase, isoamylase, or a mixture of at least one. In some embodiments, the glycolysis enzymes may be glucose amylase (glucan 1,4-alpha-glucosidase). In some embodiments, the filtrate obtained from the filtering procedure S04 is added with a 0.06% amount of starch saccharification enzymes. In some embodiments, the S05 glycolyzing procedure includes adding a 0.06% amount of a starch saccharification enzyme to the filtrate obtained from the filtering procedure 04 and then heated to and maintained at 55° C. maintained for more than 1 hour to obtain a glycolyzed solution.

In other embodiments, the S06 concentrating procedure concentrates the glycolyzed solution obtained from the glycolyzed solution S05 with reduced atmospheric pressure.

In some embodiments, after the concentrating procedure S06 is a second filtering procedure S07. The second filtering procedure S07 refers to passing the glycolyzed solution obtained by the glycolyzing procedure S06 through a 400-mesh filter to obtain the red quinoa extract. An example of an embodiment of red quinoa extract is obtained by sequentially going through the crushing procedure S01, the heating procedure S02, the filtering procedure S04, the glycolyzing procedure S05, the concentrating procedure S07, and the second filtering procedure S07.

In some embodiments, the red quinoa extract is used to prepare an antioxidant composition, wherein the red quinoa extract achieves the antioxidating effect by promoting the expression of genes related to antioxidation, and wherein the red quinoa extract is extracted with an aqueous solvent. In some embodiments, the red quinoa extract achieves the antioxidating effect by increasing antioxidant enzymes in a body.

In some embodiments, antioxidation refers to the slowing down of or the prevention of oxidation. Oxidation refers to a chemical reaction in which one or more electrons are transferred from one matter to another. This chemical reaction may generate a radical species and consequently start a chain reaction. When a chain reaction occurs in a cell, the cell will be susceptible to damage or apoptosis. In some embodiments, the red quinoa extract removes free radicals, terminate the chain reaction, or inhibits other oxidation reactions. In some embodiments, the radical species in a cell are generated due to light, chemicals, or the natural process of aging.

In some embodiments, the antioxidant-related genes include at least one of the SOD1 gene (GeneID: 6647), the SOD2 gene (GeneID: 6648), or the CAT gene (GeneID: 847).

As described above, superoxide anions, hydrogen peroxides, and other free radicals can damage skin cells. Proteins transcribed by the SOD1 gene and the SOD2 gene (superoxide dismutase) break down superoxide into hydrogen peroxide. The protein transcribed by the CAT gene breaks down hydrogen peroxide into water and oxygen. The genes transcribe proteins that are important for the removal of free radicals. Thus, the more increased is the expression of these genes in a cell, the better the cell's antioxidant capacity is.

In other words, by promoting the expression of the aforementioned antioxidation-related genes, the red quinoa extract effectively enhances cellular antioxidation capacity, improves cellular resistance to free radicals, thus protecting skin cells and improving skin condition.

In some embodiments, a concentration of 2 mg/mL of red quinoa extract promotes expression levels of antioxidation-related genes, removes free radicals, and increases cellular antioxidation capacity.

In some embodiments, a red quinoa extract having a Degrees Brix of 7.0 or more improves the expression levels of antioxidation-related genes, removes free radicals, and increases cellular antioxidation capacity.

In some embodiments, a red quinoa extract is used to prepare a skin whitening or brightening composition, wherein the red quinoa extract is achieved the skin whitening or brightening by inhibiting melanin production or inhibiting tyrosine production, wherein the red quinoa extract obtained from an aqueous solvent.

The production of melanin darkens the skin, and during the process of melanin production, tyrosinase plays a crucial role. Tyrosinase is a rate determine enzyme that regulates melanogenesis. Specifically, tyrosinase is involved in two reactions during melanin synthesis: (1) the conversion of a phenolic hydroxyl group into a single diphenol, (2) the oxidation of diphenols to quinones. The enzyme tyrosinase is present in skin melanocytes and is encoded in the TYR gene.

In some embodiments, the red quinoa extract suppresses tyrosinase formation to inhibit, prevent, or slow down melanin production in the skin, which in turn whitens or brightens the skin.

In some embodiments, a concentration of 1 mg/mL of red quinoa extract is used to whiten and brighten skin.

In some embodiments, red quinoa extract with a Degrees Brix of 7.0 or more is used to whiten and brighten skin In some embodiments, the red quinoa extract is used to prepare a skin moisturizing composition, wherein the red quinoa extract is extracted with an aqueous solvent, and wherein the red quinoa extract s extracted quinoa through ascension the amount of moisture associated gene expression to achieve the effect of moisturizing the skin.

During daily activities, the skin is prone to water loss due to the weather, the external environment, or even aging. This water loss is accelerated if the gaps between skin cells are increased. This acceleration of water loss results in the reduction of skin brightness and moisture retention capacity.

In some embodiments, moisture-related genes include the gene TGM1 (GeneID: 7051), the KRT1 gene (GeneID: 3848), the KRT10 gene (GeneID: 3858) and the gene KRT14 (GeneID: 3861).

The KRT1 gene (GeneID: 3848), the KRT10 gene (GeneID: 3858), and the KRT14 gene (GeneID: 3861) encodes the protein keratin, which helps maintain the skin's protective ability.

Specifically, the KRT1 gene, the KRT10 gene, and the KRT14 gene encode the proteins keratin 1, keratin 10, and keratin 14. Keratin is a fibrous protein that forms the main structure of keratinocytes. Keratin 1, Keratin 10, and Keratin 14 link together to form intermediate filaments that act as strong fiber networks and provide strength and elasticity to the skin. They protect the skin from friction and other physical damages and pack skin cells more closely together, resulting in the reduction of water loss via gaps between skin cells and, consequently, the skin's moisturization.

In other words, red quinoa extract promotes the expression levels of the aforementioned genes and thereby improves skin conditions.

In some embodiments, a concentration of 2 mg/mL or more of red quinoa extract enhances the skin's ability to retain moisture.

In some embodiments, a Degrees Brix of 7.0 or more of red quinoa extract enhances the skin's ability to retain moisture.

In some embodiments, the red quinoa extract is used to prepare a wrinkle soothing and/or skin texture improving composition.

In some embodiments, a concentration of more than 10 wt % of red quinoa extract smoothes out wrinkles and/or improves skin texture.

In some embodiments, a Degrees Brix of 7.0 or more of red quinoa extract enhances the skin's ability to retain moisture.

In some embodiments, the composition is a pharmaceutical composition. In other words, this pharmaceutical composition comprises an effective amount of red quinoa extract.

In some embodiments, the pharmaceutical composition can be manufactured into a medicament or formula suitable for non-parenteral or oral administration by using ordinary skills in the art. These medicaments or formulas may include, but are not limited to: tablets, troches, lozenges, pills, capsules, dispersible powders, granules, solutions, suspensions, emulsions, syrups, elixirs, slurries, or other medicaments or formulas having similar functions.

In some embodiments, the pharmaceutical composition can be manufactured into a medicament or formula suitable for non-parenteral or topical administration by using ordinary skills in the art. These medicaments or formulas include but are not limited to: injections, sterile powders, external preparations (external preparation), or other medicaments or formulas having similar functions. In some embodiments, the pharmaceutical composition may be administered through one of the following non-parenteral routes: subcutaneous injection, intraepidermal injection, intradermal injection, or intralesional injection.

In some embodiments, the pharmaceutical composition may further contain a widely used pharmaceutically acceptable carrier. In some embodiments, the pharmaceutically acceptable carrier contains one or more of the following reagents: solvents, buffers, emulsifiers, suspending agents, decomposers, disintegrating agents, dispersing agents, binding agents, excipients, stabilizers, chelating agents, diluents, gelling agents, preservatives, wetting agents, lubricants, absorption delaying agents, liposomes or other pharmaceutically acceptable carriers of similar functions. The selectio and quantification of these agents are routine practice and techniques for people having ordinary skill in the art.

In some embodiments, the pharmaceutically acceptable carrier comprises one or more of the following solvents: water, normal saline, phosphate buffered saline (PBS), an aqueous solution containing alcohol.

In some embodiments, the composition may be a food composition. In some embodiments, the food composition may be a food product or a food additive. The food additive refers to a matter that is added to manufacture a food product with conventional methods or is added during the production process of a food product. This food product can be formulated with edible materials, and the food product can be consumed by humans or animals.

In some embodiments, the food product may be but are not limited to: drinks (beverages), fermented foods, bakery products, health foods, and dietary supplements.

Example 1

Preparation of the Red Quinoa ((*Chenopodium formosanum* (Djulis))) Extract

Dried red quinoa fruits (husk included) are crushed during the crushing procedure with an Osterizer 10 speed blender. Next, the crushed dried quinoa fruits undergo the heating procedure in which water serves as the aqueous solvent. The weight ratio of the crushed dried quinoa fruits to the aqueous solvent is 1:10 and the heating procedure is maintained at 85±5° C. for 60 minutes during which the extraction takes place. Then, the solution obtained from the heating procedure is cooled to room temperature (25° C.) and is passed through a 400-mesh filter to form a filtrate. Finally, the filtrate is concentrated under sub-atmospheric pressure at 60° C. until the filtrate reaches a Degrees Brix value of 7.0±5 to give the disclosed red quinoa extract.

In some embodiments, a glycolyzing procedure is added between the filtering procedure and the concentrating procedure. That is, the filtrate is added with a 0.06% starch saccharification enzyme and undergoes a glycolyzing process at 55° C. for 1 hour to obtain a glycolyzed solution. Hereto, a commercially available AMG 300L enzyme is used as the starch saccharification enzyme.

In some embodiments, the aqueous solvent further includes an organic acid, wherein the organic acid is citric acid. The amount of citric acid is 0.05 wt % of the overall solvent.

Example 2

Quantifying Flavonoid Content

Using water, dilute the red quinoa extract obtained from EXAMPLE 1 ten-fold in terms of volume and take 200 μL of the diluted solution to a test tube. Add 5 wt % of sodium nitrite (Sigma, product No. 31443) to the test tube and allow the reaction to stand for 6 minutes.

Next, add 10 wt % of aluminum nitrate (Alfa Aesar, product No. 12360) to the test tube solution, and let the reaction stand for 6 minutes. Then, after adding 2 mL of 4 wt % aqueous sodium hydroxide (Macron, product No. 7708-10) to the solution, add 1.4 mL of water to the test tube and mix evenly to obtain the reaction solution. Take 200 μL of reaction solution into a 96-well reaction plate and detect the absorbance value at a wavelength of 500 nm using a spectrophotometer (Jasco, Model V-730).

Then, prepare standard solutions for the calibration curve: Hereto, rutin (ChromaDex, Product No. ASB-00018440) equivalents are used to express the relative content of total flavonoids. First, a concentration of 200 μg/mL of rutin methanol solution is used as the standard solution. Amounts of 0 μL, 200 μL, 400 μL, 600 μL, 800 μL, and 1000 μL of the standard solution were added to different tubes. Water is then added to the test tubes, such that the total volume of each tube is 1200 μL. Next, for the solution in each tube, 200 μL is taken to mix with 200 μL of 5 wt % aqueous sodium nitrite solution in a new test tube where the reaction is allowed to stand or 6 minutes. Followed by the addition of 200 μL 10 wt % aqueous aluminum nitrate solution, the reaction is allowed to stand for 6 minutes. Then add 2 mL of 4 wt % sodium hydroxide aqueous solution for homogenization. Next 1.4 mL of water is added to the tube and mixed to obtain a reaction solution. Finally, take 200 μL of the reaction solution into a 96-well reaction plate and detect the absorbance value at a wavelength of 500 nm using a spectrophotometer (Jasco, Model V-730). Plot the absorbance values of the six different concentrations of rutin to give a calibration curve.

The calibration curve of absorbance can be used to convert absorbance value into total flavonoid content.

Thereto, an estimation of total flavonoids of the red quinoa extract obtained from EXAMPLE 1 is 1000 ppm.

Flavonoids are not known to have the uses of improving skin condition or having antioxidative or skin whitening properties. But since it is known that flavonoids may have other uses such as the prevention of cardiovascular disease, the high total flavonoid content in the present disclosure indicates that the red quinoa extract can also have a variety of complex applications. Further, in some embodiments, the total flavonoid content can be used as an endpoint criterion for the concentrating procedure.

Example 3

Quantifying Total Polyphenol Content

Using water, dilute the red quinoa extract obtained from EXAMPLE 1 ten-fold in terms of volume and take 100 μL of the diluted solution to a test tube. Then, add 500 μL of Folin-Ciocalteu's phenol reagent (Merck, Product No. 1.09001.0100), mix well, and leave to stand for 3 minutes. Then add 400 μL of 7.5 wt % sodium carbonate (Sigma, Product No. 31432) to the test tube, mix well, and allow it to react for 30 minutes. After oscillation (Vortex) and ensuring that no air bubbles are present, take 200 μL of the solution and record its absorbance value at a wavelength of 750 nm.

Next, prepare the standard solutions to produce the calibration curve. Hereto, gallic acid equivalents are used to express the relative content of total polyphenols. Thereto, concentrations of 0 μL/mL, 20 μL/mL, 40 μL/mL, 60 μL/mL, 80 μL/mL, and 100 μL/mL of gallic acid (Sigma, product No. G7384) standard solution were made, where 100 μL of each solution were taken to a new test tube, respectively. For each test tube, 500 μL of Folin-Ciocalteu's phenol reagent is added, mixed well, and left to stand for 3 minutes. Followed by the addition of 400 μL of 7.5 wt % aqueous sodium carbonate solution, the test tube solution is mixed well and allowed to react for 30 minutes. After oscillation (Vortex) and ensuring that no air bubbles are present, take 200 μL of the solution and record its absorbance value at a wavelength of 750 nm. Plot the absorbance values of the six different concentrations of gallic acid solution to give a calibration curve.

The calibration curve of absorbance can be used to convert absorbance value into total polyphenol content. Thereto, an estimation of total polyphenols of the red quinoa extract obtained from EXAMPLE 1 is 400 ppm.

Polyphenols are not known to have the uses of improving skin condition, or having antioxidative or skin whitening properties. But since it is known that polyphenols may have other uses such as the prevention of cardiovascular disease, the high total polyphenol content in the present disclosure indicates that the red quinoa extract can also have a variety of complex applications. Further, in some embodiments, the total polyphenol content can be used as an endpoint criterion for the concentrating procedure.

Example 4

Inhibition of Tyrosine Production

Tyrosinase has a key role in the synthesis of melanin. Tyrosinase catalyzes the conversion of tyrosine to L-Dopa, which is further produced into Dopaquinone and then to melanin. Thus, by detecting the activity of tyrosinase, melanocytes' ability to produce melanin can be inferred. When the activity of tyrosinase is low, the melanin production capacity of melanocytes is relatively reduced.

Materials and Equipment
1. Cell line: B16F10 mouse melanoma cells, purchased from American Type Culture Collection (American Type Culture Collection, ATCC®, No. 6475), hereinafter referred to as B16F10 cells.
2. Cell culture medium: Basal medium containing 10 vol % FBS (fetal bovine serum, available from Gibco), wherein the basal medium is Eagle's minimum essential medium (MEM) (Gibco, Catalog No. 15188-319) with the addition of 1 mM sodium pyruvate (Gibco), 1.5 g/L sodium bicarbonate (Sigma), and 0.1 mM non-essential amino acid solution (Gibco).
3. Phosphate Buffered Saline solution (PBS solution): purchased from Gibco, Catalog No.: 10437-028.
4. Kojic acid: purchased from Sigma-Aldrich, product No. K3125-5G.
5. Radioimmunoprecipitation protein lysis buffer (RIPA Lysis Buffer (PMSF)): purchased from Sigma-Aldrich, product No. 10837091001.
6. Bio-rad Protein Assay: available from Biotek, Item Epoch.
7. 10 mM L-dopa: obtained by dissolving 9.8 mg of L-dopa (Sigma-Aldrich, product No. D9628-5G) into 5 mL of 0.1 mM, pH 7.0 PBS.
8. Trypsin: 10× Trypsin-EDTA (Gibco) diluted 10-fold in 1×PBS solution.
9. Red quinoa extract: prepared by the method detailed in EXAMPLE 1.

Experimental Procedure:

Seed $1.5 \times 10^5$ B16F10 cells with 2 mL of medium in each well of a 6-well plate and incubate at 37° C. for 24 hours.

Then, carefully remove the culture medium without interfering with the attachment of cells.

This experiment is divided into three groups: the control group, experimental group A, and experimental group B. The control group is added with 2 mL of fresh medium and incubated for 48 hours; experimental group A is added with 2 mL of 1 mg/mL red quinoa extract and incubated for 48 hours; experimental group B is added with 2 mL of 0.5 mg/mL red quinoa extract, and incubated for 48 hours. The red quinoa extract samples in experimental groups A and B were obtained by mixing 2 mL of medium with 14.3 μL and 28.6 μL of the red quinoa extract prepared from EXAMPLE 1.

Subsequently, the medium is removed and washed with 1×PBS (Gibco) twice. Trypsin-EDTA was added to the wells and to react for 3 minutes. The cells were then retrieved from the suspension and taken into 15 mL centrifuge tubes, where they were centrifuged for 5 minutes at 400×g to pellet the cells.

Then, the precipitated cells were washed twice with 1×PBS, suspended with 200 μL cell lysate, vortexed, and centrifuged for 20 min at 12,000×g.

Transfer the supernatant to 1.5 mL centrifuge tubes, where the protein concentrations are detected:

Bio-rad dye is mixed with deionized water (volume ratio 1:4) and distributed into 7 microcentrifuge tubes, each having 500 μL of the solution. Then, the microcentrifuge tubes were added with 10 μL, 8 μL, 6 μL, 4 μL, 2 μL, 1 μL, and 0 μL of 2 mg/mL BSA, respectively to prepare the standard protein concentration sample. Next, 2 μL of supernatant is added to each microcentrifuge tube for testing. The microcentrifuge tubes were then added to the wells of a 96 well plate where each well is added with 200 μL of protein assay reagent. Then, the absorbance value was measured at 595 nm using the ELISA reader (BioTek).

Next, 400 µg of protein is added to each well. Then, 90 µL cell lysate is added to each well, including the control group. Under a dark environment, add 10 µL 10M of L-Dopa at 37° C. and observe the suspension once every 10 minutes, until the suspension turns black. Then, measure the absorbance value at 405 nm.

Tyrosinase inhibition is calculated with the following formula:

Tyrosinase Inhibition (%)=(OD sample/OD control)× 100%.

The results are then analyzed with Microsoft EXCEL software using its Student t-test statistical analysis.

Figure 3:
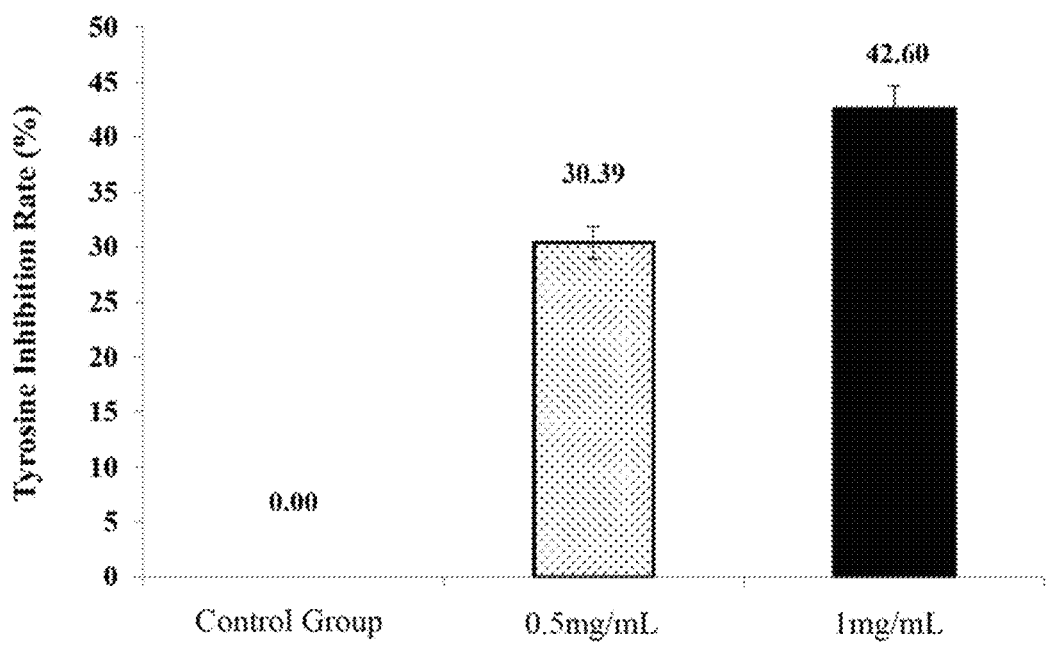
FIG. 3 shows the tyrosine inhibition ratios of the experimental and control groups in EXAMPLE 4.

Referring to FIG. 3, the tyrosinase inhibition is improved in the group containing the red quinoa extract and increases with the red quinoa extract concentration. Specifically, experimental group B (0.5 mg/mL of red quinoa extract) has a 30.4% higher tyrosine inhibition rate than experimental group A (1 mg/mL of red quinoa extract), which has a 42.6% higher tyrosine inhibition rate than the control group. Thus, the red quinoa extract disclosed herein reduces tyrosinase activity, which, in turn, reduces the formation of melanin. This shows that the red quinoa extract disclosed here can be used to reduce skin spots, improve skin condition, whiten the skin.

Example 5

Reduction of Melanin Content

This example demonstrates the melanin content reducing capability of the red quinoa extract disclosed herein by quantifying the difference in melanin content after treating B16F10 melanoma cells with the red quinoa extract disclosed herein with ELISA reader (enzyme-linked immunosorbent assay reader).

Materials and Equipment
1. Cell line: B16F10 mouse melanoma cells, purchased from American Type Culture Collection (American Type Culture Collection, ATCC®, No. 6475), hereinafter referred to as B16F10 cells.
2. Cell culture medium: Basal medium containing 10 vol % FBS (fetal bovine serum, available from Gibco), wherein the basal medium is Eagle's minimum essential medium (MEM) (Gibco, Catalog No. 15188-319) with the addition of 1 mM sodium pyruvate (Gibco), 1.5 g/L sodium bicarbonate (Sigma), and 0.1 mM non-essential amino acid solution (Gibco).
3. Phosphate Buffered Saline solution (PBS solution): purchased from Gibco, Catalog No.: 10437-028.
4. 1N NaOH (Sigma, Product No. 221465).
5. ELISA reader (BioTek, FLx 800).
7. Blue Light (wavelength: 400 nm-500 nm).
6. Red quinoa extract: prepared from EXAMPLE 1.

Experimental Procedure

This experiment is divided into two groups with three replicates: the experimental group and the control group:
1. Seed $1.5 \times 10^5$ B16F10 cells with 2 mL of medium in each well of a 6-well plate.
2. Incubate plate at 37° C. for 24 hours.
3. Carefully remove culture medium without interfering with attachment of cells.
4. The experimental group is added with 2 mL of 0.5 mg/mL red quinoa extract and incubated for 48 hours. The red quinoa extract sample was obtained by mixing 2 mL of medium with 14.3 µL of the red quinoa extract prepared from EXAMPLE 1.

The control group is added with 2 mL of fresh medium and incubated for 48 hours.
5. The experimental group is exposed to blue light at room temperature (25±5° C.) for 3 hours.

The control group is moved to a dark room and allowed to stand at room temperature for 3 hours.
6. Next, incubate cells at 37° C. for 48 hours.
7. The culture medium is removed and the cells were washed with PBS solution two times.
8. 200 µl Trypsin-EDTA (10×) (Gibco; Catalog No. 15400-054) is added to each well for 3 minutes. Then, 6 mL of culture medium is added to terminate the reaction. Collect the suspended cells to a 15 ml centrifuge tube and centrifuge at 400 xg for 5 minutes to pellet the cells.
9. After washing with PBS twice, resuspended the cells with 200 µL PBS.
10. The cell suspension is frozen in liquid nitrogen for 10 minutes and then left at room temperature for about 30 minutes until completely thawed.
11. After thawing is complete, the tubes were centrifuged at 12,000 g for 3 minutes.
12. After removing the supernatant, use 120 µL of 1N sodium hydroxide solution to precipitate the cells and put the test tube in a hot plate at 60° C. for 1 hour to obtain samples for detection.
13. Take 100 µL of the sample into a 96-well plate, and measure optical density at 450 nm with the ELISA reader.

Experimental Results

Melanin content of the groups are calculated with the following formula:

Melanin Content (%)=OD450 Experimental/OD450 Control)×100%.

Figure 4:
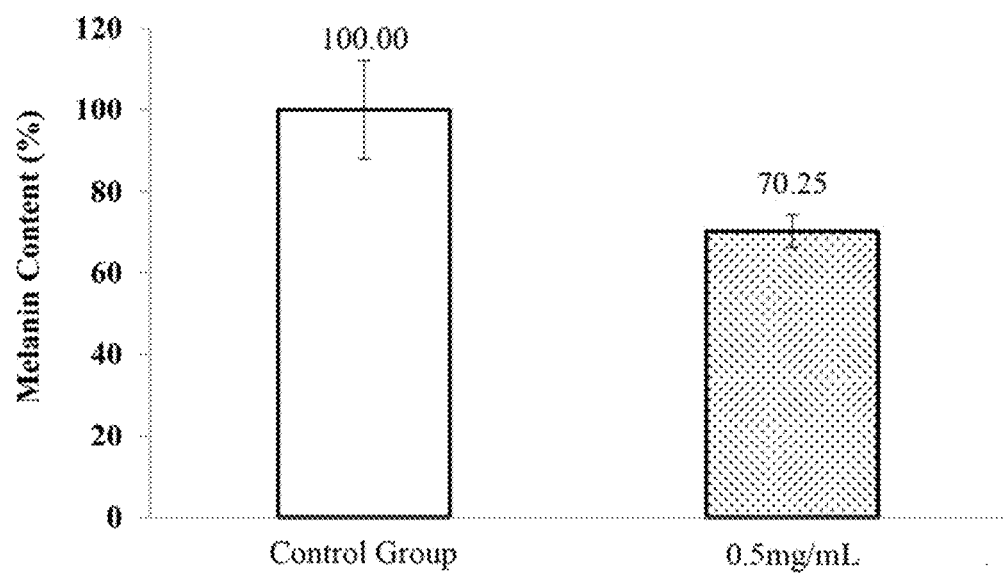
FIG. 4 shows the melanin production ratios of the experimental and control groups in EXAMPLE 5.

Since the experiment was carried out in triplets, the values were averaged, as shown in FIG. 4.

As shown in FIG. 4, the melanin content of the experiment group is 29.7% lower than the control group, indicating that the red quinoa extract disclosed herein has can effectively reduce the production of melanin in melanocytes.

Example 6

Enhanced Expression of Antioxidation-Related Genes

This example uses an RNA extraction kit, reverse transcriptase, a KAPA SYBR® FAST qPCR reagent kit, and quantitative PCR to determine the expression of antioxidation-related genes in human skin fibroblasts (CCD-966sk) after being treated by the red quinoa extract disclosed herein.

Materials and Equipment
1. Cell line: Human skin fibroblasts CCD-966sk (BCRC No. 60153).
2. Cell culture medium: Basal medium containing 10 vol % FBS (fetal bovine serum, available from Gibco), wherein the basal medium is Eagle's minimum essential medium (MEM) (Gibco, Catalog No. 15188-319) with the addition of 1 mM sodium pyruvate (Gibco), 1.5 g/L sodium bicarbonate (Sigma), and 0.1 mM non-essential amino acid solution (Gibco).
3. RNA extraction reagent kit (Geneaid, Taiwan, Lot No. FC24015-G).
4. Reverse Transcriptase (SuperScript® III Reverse Transcriptase) (Invitrogen Corporation, USA, No. 18080-051).
5. Target gene primers: the SOD2 gene and the GAPDH gene (internal control group).

6. KAPA SYBR® FAST qPCR reagent set (purchased from Sigma, USA, No. 38220000000)
7. ABI StepOnePlus™ Real-Time PCR system (Thermo Fisher Scientific Inc., USA).
8. Red quinoa extract: prepared from EXAMPLE 1.

Experimental Procedure

The cell culture experiment process is as follows:
This experiment is divided into two groups with three replicates: the experimental group and the control group:
1. Seed $1.5 \times 10^5$ CCD-966sk cells with 2 mL of medium in each well of a 6-well plate and incubate at 37° C. for 16 hours.
2. Experimental group: per ml culture broth containing a red-quinoa extract prepared 28.6 μL of a sample obtained by the embodiment (i.e., at a concentration of 1 mg/mL) is prepared to contain extract broth, the CCD-966sk cell extracts containing replaced broth culture is continued.
3. The experimental group is added with 2 mL of 1 mg/mL red quinoa extract and incubated for 6 hours. The red quinoa extract sample was obtained by mixing 2 mL of medium with 28.6 μL of the red quinoa extract prepared from EXAMPLE 1.

The control group is added with 2 mL of fresh medium and incubated for 6 hours
4. After incubation, lysate the cells of both the experimental and control groups using the reagents provided in the RNA extraction kit.

The polymerase chain reaction experiment process is as follows:
a. Collect the RNA of the cells in both groups using the RNA extraction kit.
b. Next, take 2000 nanograms (ng) of the RNA extracted in each group as a template, and use the primers listed in Table 1 to reverse-transcribe cDNA using SuperScript® III reverse transcriptase.
c. Use the primers in Table 1 to conduct quantitative real-time reverse transcription polymerase chain reaction with StepOnePlus™ Real-Time PCR system and KAPA SYBR FAST. This allows the observation of the gene expression levels of the experimental group and the control group. The parameters for the PCR are 95° C./1 s, 60° C./20 s, 40 loops
d. The relative gene expression levels are determined by the $2^{-\Delta\Delta Ct}$ method. The "relative gene expression levels" are defined as the fold change of the experimental group's RNA expression level to that of the control group. The GADPH gene is served as the internal control of the reference gene cycle threshold (Ct). Fold change is calculated according to the following formula:

$$\Delta Ct = Ct_{experimental\ group\ target\ gene/control\ group\ target\ gene} - Ct_{TBP}$$

$$\Delta\Delta Ct = \Delta Ct\ of\ experimental\ group - \Delta Ct\ gene\ of\ the\ control\ group$$

$$Fold\ change = 2^{-\Delta\Delta Ct}\ average$$

5. Finally, the standard deviation and a one-tailed Student t-test analysis are conducted with Microsoft Excel to determine whether a significant difference exists (* p value<0.05 statistically;  p value<0.01; * p value<0.001). The SOD2 gene's corresponding primer is SOD2-F and SOD2-R while the gene corresponding to the GADPH is GADPH-F primers and GADPH-R.

TABLE 1

| Primer | Sequence No. | Sequence |
|---|---|---|
| SOD2-F | SEQ ID NO: 1 | AGAGTGGACCAACTGAAGAGT |
| SOD2-R | SEQ ID NO: 2 | ATTCTCTGCATTTGTCCGCTT |
| GADPH-F | SEQ ID NO: 3 | TCCTACTTGGACAAAGTTCGGG |
| GADPH-R | SEQ ID NO: 4 | CCCCTGATGTGAGTTGCCA |

Experimental Results

Figure 5:
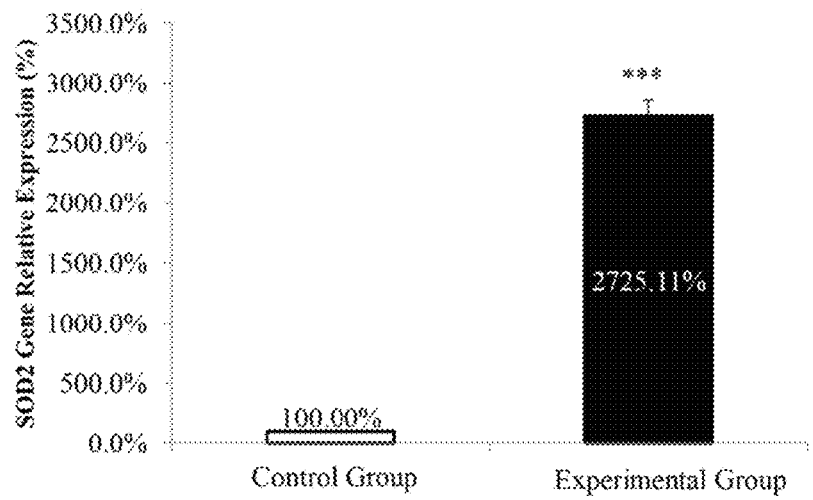
FIG. 5 shows the gene expression ratios of the antioxidant-related genes in the experimental and control groups in EXAMPLE 6.

FIG. 5. shows the relative expression levels of the antioxidation-related genes of the experiment and control group.

From FIG. 5, the relative expression level of the SOD2 gene in the experimental group is 2725%. In other words, compared with the control group, the expression level of the antioxidation-related SOD2 gene in the experimental group increased 2625%, reaching statistical significance. Thus, the red quinoa extract disclosed herein has free radical scavenging properties and can function as an antioxidant.

Example 7

Enhanced Expression of Moisture-Related Genes

This example uses an RNA extraction kit, reverse transcriptase, a KAPA SYBR® FAST qPCR reagent kit, and quantitative PCR to determine the expression of moisture-related genes in human epidermal keratinocytes (HPEK-50) after treatment of the red quinoa extract disclosed herein.

Materials and Equipment
1. Keratinocyte serum-free medium (Keratinocyte-SFM; available from Thermo, part number 17005042).
2. Human epidermal keratinocytes (hereinafter as HPEK-50 cells or keratinocytes; available from CELLnTEC).
3. RNA extraction reagent kit (Geneaid, Taiwan, Lot No. FC24015-G).
4. Reverse Transcriptase (SuperScript® III Reverse Transcriptase) (Invitrogen Corporation, USA, No. 18080-051).
5. Target gene primers: the TGM1 gene, the KRT1 gene, the KRT10 gene, and the TBP gene (internal control group).
6. KAPA SYBR® FAST qPCR reagent set (purchased from Sigma, USA, No. 38220000000)
7. ABI StepOnePlus™ Real-Time PCR system (Thermo Fisher Scientific Inc., USA).
8. Red quinoa extract: prepared from EXAMPLE 1.

Experimental Procedure

The cell culture experiment process is as follows:
This experiment is divided into two groups with three replicates: the experimental group and the control group:
1. Seed $1.5 \times 10^5$ HPEK-50 cells with 2 mL of medium in each well of a 6-well plate and incubate at 37° C. for 16 hours.
2. The experimental group is added with 2 mL of 2 mg/mL red quinoa extract, and incubated for 6 hours. The red quinoa extract sample was obtained by mixing 2 mL of medium with 57.2 μL μL of the red quinoa extract prepared from EXAMPLE 1.

The control group is added with 2 mL of fresh medium and incubated for 6 hours
3. After incubation, lysate the cells of both the experimental and control groups using the reagents provided in the RNA extraction kit.
4. The polymerase chain reaction experiment process is as follows:

a. Collect the RNA of the cells in both groups using the RNA extraction kit.
b. Next, take 2000 nanograms (ng) of the RNA extracted in each group a template, and use the primers listed in Table 1 to reverse transcribe cDNA using SuperScript® III reverse transcriptase.
c. Use the primers in Table 2 to conduct quantitative real-time reverse transcription polymerase chain reaction with StepOnePlus™ Real-Time PCR system and KAPA SYBR FAST. This allows the observation of the gene expression levels of the experimental group and the control group. The parameters for the PCR are: 95° C./1 s, 60° C./20 s, 40 loops
d. The relative gene expression levels are determined by the $2^{-\Delta\Delta Ct}$ method. The "relative gene expression levels" are defined as the fold change of the experimental group's RNA expression level to that of the control group. The TBP gene is served as the internal control of the reference gene cycle threshold (Ct). Fold change is calculated according to the following formula:

$$\Delta Ct = Ct_{experimental\ group\ target\ gene/control\ group\ target\ gene} - Ct_{TBP}$$

$$\Delta\Delta Ct = \Delta Ct\ of\ experimental\ group - \Delta Ct\ gene\ of\ the\ control\ group$$

$$Fold\ change = 2^{-\Delta\Delta Ct}\ average$$

5. Finally, the standard deviation and a one-tailed Student t-test analysis is conducted with Microsoft Excel to determine whether a significant difference exists (* p value<0.05 statistically;  p value<0.01; * p value<0.001). The TGM1 gene's corresponding primer pair is TGM1-F and TGM1-R, the KRT1 gene's corresponding primer pair is KRT1-F and KRT1-R, the KRT10 gene's corresponding primer pair is KRT10-F and KRT10-R, the TBP gene's corresponding primer pair is TBP-F and TBP-R.

TABLE 2

| Primer | Sequence No. | Sequence |
| --- | --- | --- |
| TGM1-F | SEQ ID NO: 5 | GATCGCATCACCCTTGAGTTAC |
| TGM1-R | SEQ ID NO: 6 | GCAGGTTCAGATTCTGCCC |
| KRT1-F | SEQ ID NO: 7 | AGAGTGGACCAACTGAAGAGT |
| KRT1-R | SEQ ID NO: 8 | ATTCTCTGCATTTGTCCGCTT |
| KRT10-F | SEQ ID NO: 9 | TCCTACTTGGACAAAGTTCGGG |
| KRT10-R | SEQ ID NO: 10 | CCCCTGATGTGAGTTGCCA |
| TBP-F | SEQ ID NO: 11 | TATAATCCCAAGCGGTTTGC |
| TBP-R | SEQ ID NO: 12 | GCTGGAAAACCCAACTTCTG |

Experimental Results

Figure 6:
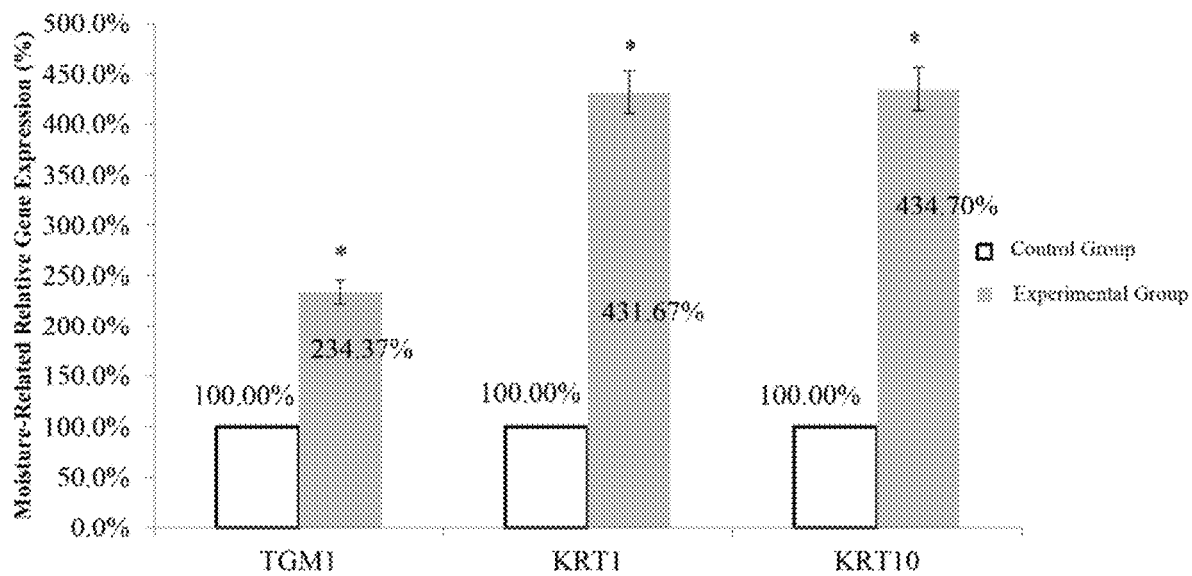
FIG. 6 shows the gene expression ratios of the moisturizing-related genes in t the experimental and control groups in EXAMPLE 7.

FIG. 6. shows the relative expression levels of the moisture-related genes of the experiment and control group.

From FIG. 5, the relative expression levels of the TGM1 gene, the KRT1 gene, and the KRT10 gene are 234%, 432% and 435%, respectively. In other words, compared with the control group, the expression level of the TGM1 gene, the KRT1 gene, and the KRT10 gene in the experimental group increased 134%, 332%, and 335%, respectively, all reaching statistical significance. Thus, the red quinoa extract disclosed herein can prevent skin water loss, moisturize the skin and improve skin function.

Example 8

Clinical Trials—Antioxidation and Skin Condition Improvement

This example demonstrates the antioxidation and skin condition, improving properties of the red quinoa extract disclosed herein by administering drinks containing the red quinoa extract disclosed in the present invention to human subjects.

Drinking Sample: Beverage containing the presently disclosed red quinoa extract 50 g/bottle, which comprises: red quinoa extracted 10 wt %, apple juice concentrate 6 wt %, fructose 6 wt %, 0.4 wt % citrus pectin, citric acid 0.2 wt %, apple liquid spices 0.24 wt %, water 77.16 wt %. In other embodiments, the intake of red quinoa extract can be up to 10 g/day. The red quinoa extract herein is produced with the method detailed in EXAMPLE 1. It should be noted that the concentrated apple juice 6 wt %, fructose 6 wt %, citrus pectin 0.4 wt %, citric acid 0.2 wt %, apple liquid spices 0.24 wt % are meant to flavor and to enhance the shelf life of the beverage.

Number of subjects: 30 subjects, 30-55 years of age.
Experimental Procedure

1. Collect 30 subjects. Before drinking the beverages, the subjects' skin conditions (face cleaned, week 0) using the corresponding instruments. Blood samples of the subjects were also collected (under fasting conditions) to measure the content of antioxidant enzymes in the body.
2. Next, randomly select 15 subjects as the placebo group and the remaining 15 as the experimental group. The experimental group takes a bottle of the beverage daily (containing 5 g of red quinoa extract) for a total of 56 days (i.e., 8 weeks). The placebo group takes placebo beverages (same content as the beverage drunk by the experimental group only that the 5 g red quinoa extract was substituted with an equal amount of water).
3. The skin conditions of the subjects in the placebo group and the experimental groups were measured at week 0, week 4, and week 8. Their blood samples were also collected at week 0, week 4, and week 8. It should be noted that the temperature, humidity, and other environmental factors of where the measurements took place were the same at week 0, week 4, week 8 so as to reduce the impact of other factors on the skin condition measurements. Moreover, during the clinical trial, the subjects' diets and lifestyles were unchanged so as to reduce other factors that may impact the content of in vivo antioxidants.

Measurements
1. Skin Hydration, 2. Skin color, 3. Skin texture, 4 Crow's feet, 5. Antioxidant Enzyme Content
1. Skin Hydration Purchased from the German company Courage+Khazaka electronic, the skin hydration probe Corneometer® CM825 (C+K MµLti Probe Adapter System, Germany) is used to detect facial skin hydration in both groups. The values of the detection probe are based on capacitive measurement. Since the capacitance value of the skin changes with the skin's hydration, the detection probe can analyze skin hydration by measuring skin capacitance values.

2. Skin Color

Purchased from the Irish company Miravex, the 3D analytical lens of Antera 3D is used to detect facial skin color in both groups. The instrument first emits lights using its LED (light-emitting diodes) at different wavelengths and angles and then collects the reflected lights that bounce off of the skin to analyze the skin color. Antera uses colorimeter to analyze color, which depends on the parameters L*a*b* in which L* refers to brightness; the a* axis represents the green-red component, with green in the negative direction and red in the positive direction; the b* axis represents the blue-yellow component, with blue in the negative direction and yellow in the positive direction.

For the difference ($\Delta E_{ab}*$) in color 1 ($L_1*$, $a_1*$, $b_1*$) and color 2 ($L_2*$, $a_2*$, $b_2*$) can be calculated by the following formula:

$$\Delta E_{ab}* = \sqrt{(L_2*-L_1*)^2 + (a_2*-a_1*)^2 + (b_2*-b_1*)^2}$$

Since this example mainly concerns the whitening of the skin, only the L* value is observed and recorded. The higher the L* value is, the brighter and hence the whiter the skin is.

3. Skin Texture

Skin texture is measured using the VISTA Digital Skin Detector (Canfield, US).

The instrument uses visible light to capture high-resolution images of the skin and uses its built-in software to analyze skin roughness. The higher the measured value is, the rougher the skin is.

4. Crow's Feet Measurement

The Soft Plus Skin Detector (Callegari 1930) is used to measure the end of the subjects' eyes to evaluate crow's feet. The instrument detects the area of shades against standard light to quantify the depth of crow's feet.

5. Antioxidant Enzymes Measurement

First, the collected blood samples were transferred into a centrifuge tube and centrifuged at 700-1000×g, 4° C. for 10 minutes. After centrifugation, the upper plasma layer is removed, and 2 mL of the blood cell layer (i.e., buffy coat) is placed in another centrifuge tube where 2 mL of PBS is added and mixed to provide a diluted buffy coat.

Add 3 mL of the diluted buffy coat into another test tube and slowly add Ficoll-Plague Plus solution (Sigma), and then centrifuged at a rotational speed of 400 g for 40 minutes. After centrifugation, remove the supernatant liquid and transfer 2 mL-3 mL of the intermediate layer (i.e., the mononuclear cell layer) to a new centrifuge tube.

After washing the mononuclear cells with PBS 3 to 5 times, centrifuge it for 10 minutes with 300 g. After centrifugation, the supernatant is the sample used for subsequent experiments.

Reference to the instructions provided by the Cayman Catalase Assay Kit No. 707002 (https://www.caymanchem.com/pdfs/707002.pdf). A summarized procedure is presented as follows:

Mix 10 μL of the standardized hydrogen peroxide formaldehyde enzyme (Cayman, No. 707014) with a buffer solution of 9.99 mL to obtain a formaldehyde solution of 4.25 mM. Take 7 tubes and label them from A through G and formulate them according to Table 3 to give the standard solutions:

TABLE 3

| Test Tube | Formaldehyde (μL) | Buffer Solution (μL) | Final Formaldehyde Concentration (μM) |
|---|---|---|---|
| A | 0 | 1000 | 0 |
| B | 10 | 990 | 5 |
| C | 30 | 970 | 15 |
| D | 60 | 940 | 30 |
| E | 90 | 910 | 45 |
| F | 120 | 880 | 60 |
| G | 150 | 850 | 75 |

This experiment is divided into three groups: the standard formaldehyde group, the positive control group, and the experimental group. The standard formaldehyde group takes up seven wells, wherein each well contains 100 μL of buffer solution, 30 L of methanol, and 20 μL of the standard solution (tube A to G); the positive control group takes up two wells, wherein each well contains 100 μL of buffer solution, 30 L of methanol, and 20 μL of the diluted antioxidant enzymes; while the experimental group wells contain 100 μL of buffer solution, 30 μL of methanol and 20 μL of the experimental samples (i.e., the processed blood samples).

Add 20 μL of hydrogen peroxide to each well to start the reaction, and then the wells were shaken at room temperature for 10 minutes.

Next, 30 μL of potassium hydroxide is added to terminate the reaction, and a 304, of dye (Catalase Purpalf, Cayman No. 707017) is added to each well. The wells were then shaken at room temperature for 10 minutes.

Then, add 104, Catalase Potassium Periodate (Cayman No. 707017) and shake wells at room temperature after 5 minutes.

Finally, read the absorbance values at 540 nm wavelength.

Catalase Content is calculated as follows:

First, subtract the absorbance values of each sample with the absorbance value of standard solution A and then plot the subtracted values. The y-axis is the absorbance value (540 nm), while the x-axis is the concentration of formaldehyde (μM). The calculation of the formaldehyde concentration of the experimental group of:

Formaldehyde concentration (μM)=((absorbance value of experimental group−y-intercept of the drawing made)/slope of the drawing made)× (0.17 mL/0.02 mL)

Then calculate the enzyme activity of catalase:

Catalase activity=(sample formaldehyde concentration (μm))/(20 min)×dilution ratio experiment=nmol/min/mL The catalase content is set at 100% at week 0 for both the placebo and control group to better present the relative catalase content of the groups.

Figure 7:
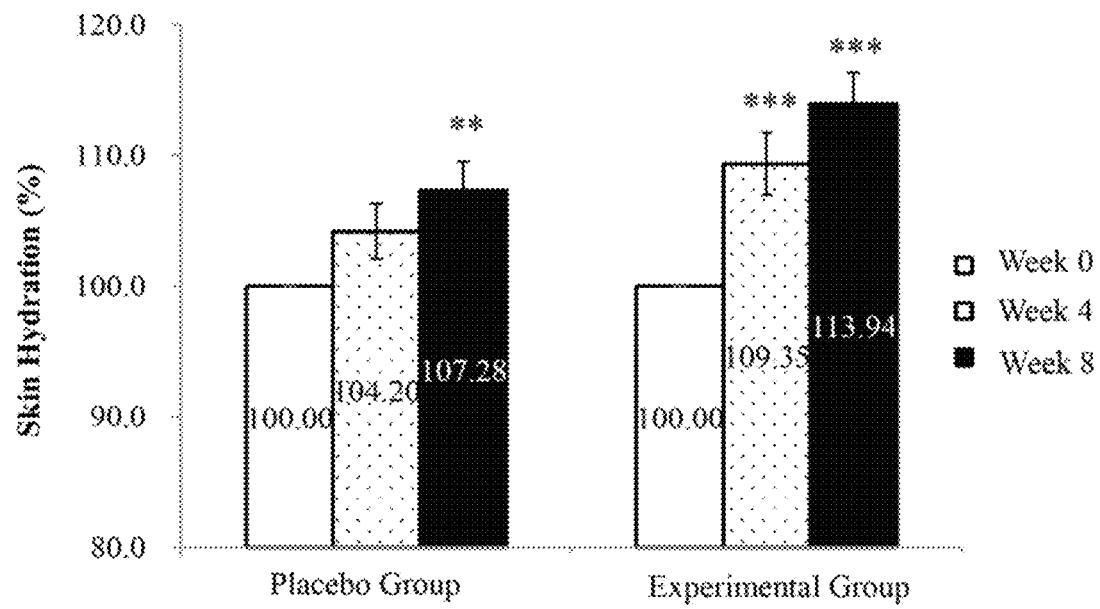
FIG. 7 shows skin moisture retention ratios of the experimental and placebo groups in EXAMPLE 8 after intake of health drinks with and without the red quinoa extract, respectively, for 4 weeks and 8 weeks.

FIG. 7. shows the average skin hydration percentage at week 0, week 4, and week 8 of the placebo group and the experiment group. At week 4, 93% of the subjects had an increase in skin hydration, whereas, at week 8, 100% of the subjects had an increase in skin hydration. When the test subjects' average skin hydration percentage before beverage consumption is 100%, the average skin hydration percentage after 4 weeks of consumption is 109.3%, while the average skin hydration percentage after 8 weeks of consumption is 113.9%. In other words, the subjects in the experimental group had an average increase of 9.3% and 13.9% in skin hydration, respectively, both reaching statistical significance. The average skin hydration percentages of the experiment group in week 4 and week 8 were also higher than those of the placebo group in week 4 and week 8 by 5.1% and 6.6%, respectively. Thus, the present disclosed red quinoa extract can be used to moisturize the skin and maintain skin moisture retention.

Figure 8:
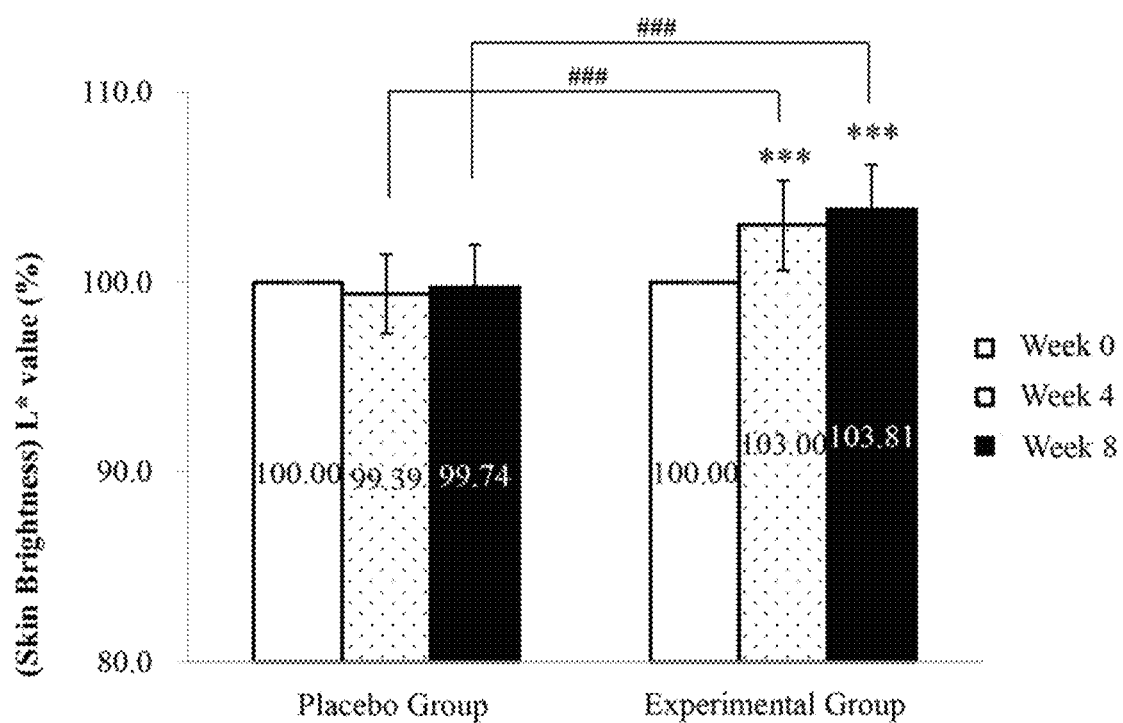
FIG. 8 shows skin whiteness ratios of the experimental and placebo groups in EXAMPLE 8 after intake of health drinks with and without the red quinoa extract, respectively, for 4 weeks and 8 weeks.

FIG. 8. shows the average skin color percentage at week 0, week 4, and week 8 of the placebo group and the experiment group. At week 4, 93% of the subjects had an increase in skin color, whereas, at week 8, 100% of the subjects had an increase in skin color. When the test subjects' average skin color percentages before beverage consumption are 100%, the average skin color percentage after 4 weeks of consumption is 103.0%, while the average skin color percentage after 8 weeks of consumption is 103.8%. In other words, the subjects in the experimental group had an average increase of 3.0% and 3.8% in skin color, respectively, both reaching statistical significance. The average skin color percentages of the experiment group in week 4 and week 8 were also higher than those of the placebo group in week 4 and week 8 by 3.6% and 4.1%, respectively. Thus, the present disclosed red quinoa extract can be used to brighten and whiten skin color.

Figure 9:
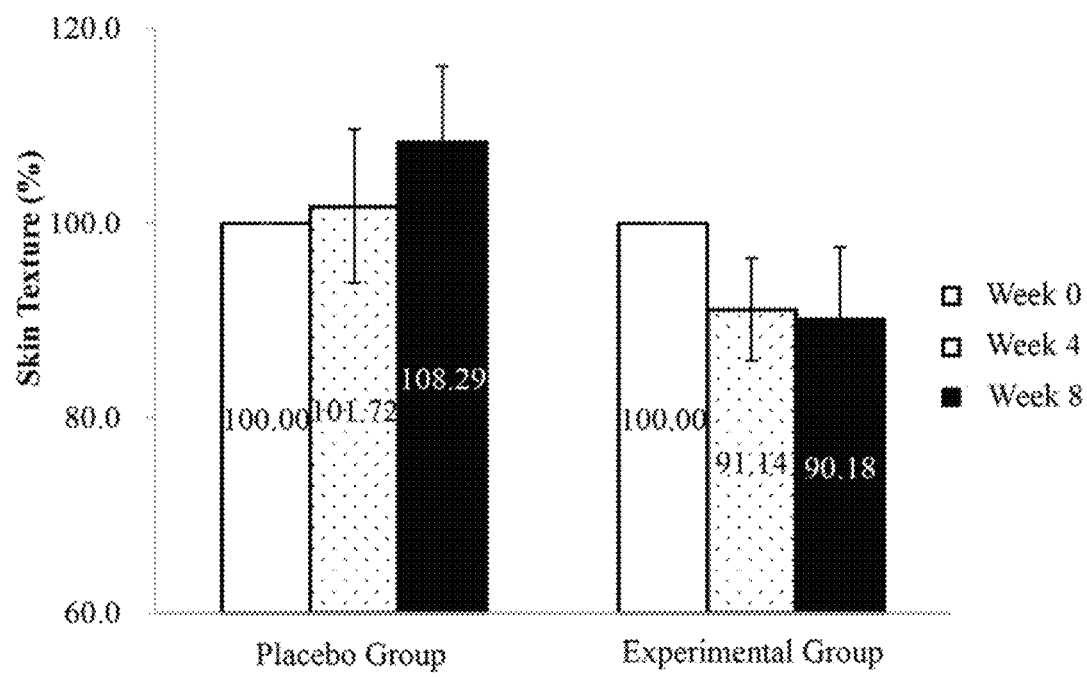
FIG. 9 shows skin texture ratios of the experimental and placebo groups in EXAMPLE 8 after intake of health drinks with and without the red quinoa extract, respectively, for 4 weeks and 8 weeks.
Figure 10:
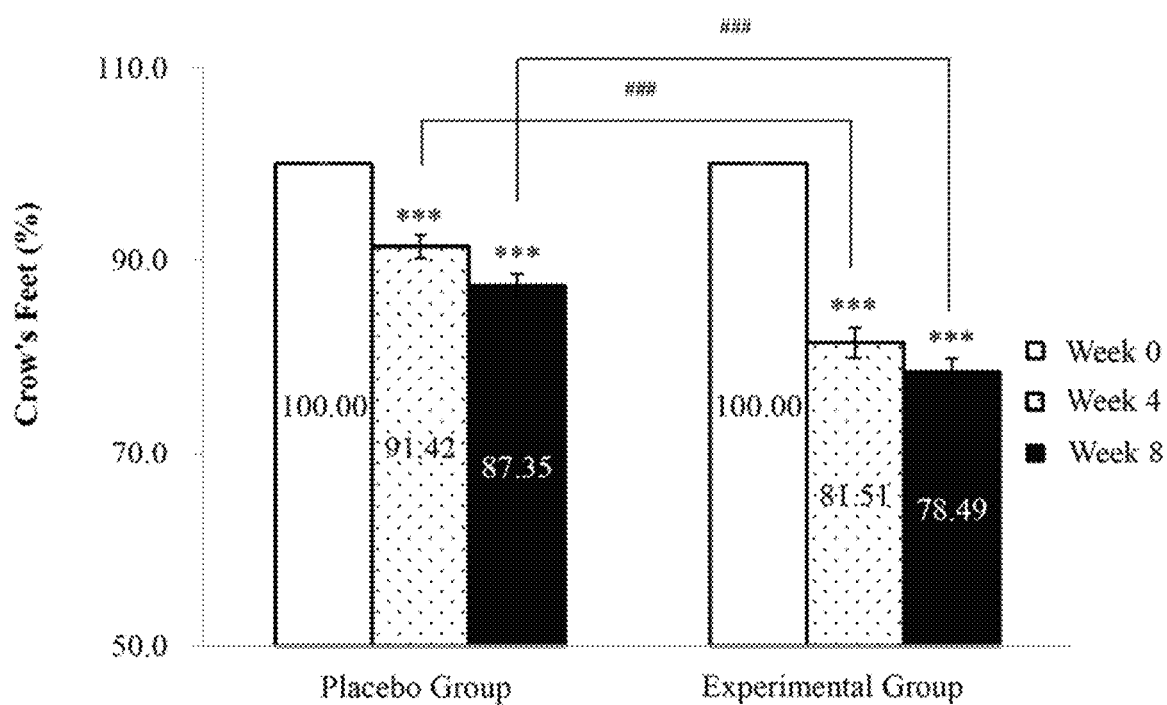
FIG. 10 shows crow's feet proportions of the experimental and placebo groups in EXAMPLE 8 after intake of health drinks with and without the red quinoa extract, respectively, for 4 weeks and 8 weeks.
Figure 11:
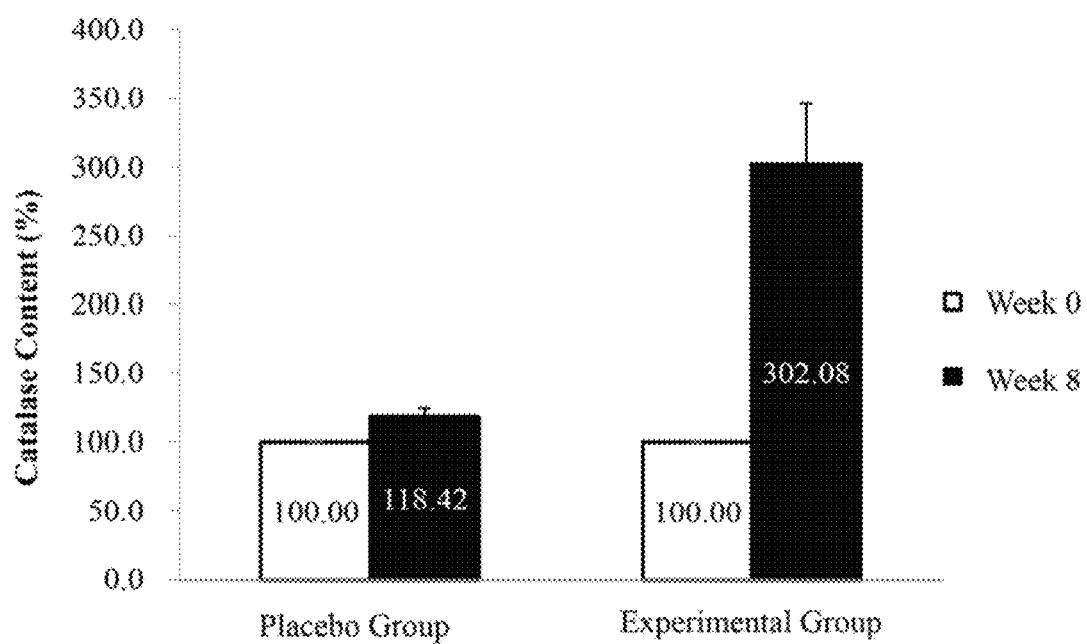
FIG. 11 shows the amount of antioxidant enzyme present in the bodies of the experimental and placebo groups in EXAMPLE 8 after intake of health drinks with and without the red quinoa extract, respectively, for 4 weeks and 8 weeks.

FIG. 9. shows the average skin texture percentage at week 0, week 4, and week 8 of the placebo group and the experiment group. At week 4, 73% of the subjects had an increase in skin texture, whereas, at week 8, 83% of the subjects had an increase in skin texture. When the test subjects' average skin texture percentage before beverage consumption is 100%, the average skin texture percentage after 4 weeks of consumption is 91.1%, while the average skin texture percentage after 8 weeks of consumption is 90.2%. In other words, the subjects in the experimental group had an average decrease of 8.9% and 9.8% in skin texture, respectively. The average skin texture percentages of the experiment group in week 4 and week 8 were also lower than those of the placebo group in week 4 and week 8 by 10.6% and 18.1%, respectively. Thus, the present disclosed red quinoa extract can be used to improve skin texture and reduce the roughness of the skin FIG. 10. shows the average crow's feet percentage at week 0, week 4, and week 8 of the placebo group and the experiment group. At both week 4 and week 8, 100% of the subjects had a decrease in crow's feet percentage. When the test subjects' average crow's feet percentage before beverage consumption is 100%, the average crow's feet percentage after 4 weeks of consumption is 81.5%, while the average crow's feet percentage after 8 weeks of consumption is 78.5%. In other words, the subjects in the experimental group had an average decrease of 18.5% and 21.5% in crow's feet, respectively, both reaching statistical significance. The average crow's feet percentages of the experiment group in week 4 and week 8 were also lower than those of the placebo group in week 4 and week 8 by 9.9% and 8.9%, respectively. Thus, the present disclosed red quinoa extract can be used to soothe wrinkles FIG. 11. shows the average in vivo antioxidant enzyme (catalase) percentage at week 0, week 4, and week 8 of the placebo group and the experiment group. At week 8, 100% of the subjects had an increased catalase percentage. When the test subjects' average catalase percentage before beverage consumption is 100%, the average catalase percentage after 8 weeks of consumption is 302.1%. In other words, the subjects in the experimental group had an average increase of 202.1% in catalase percentage, reaching statistical significance. The average catalase percentages of the experiment group in week 8 were also higher than those of the placebo group in week 8 by 183.7%. Thus, the present disclosed red quinoa extract can be used to enhance the content of antioxidant enzymes, thereby achieving antioxidative properties in vivo.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for skin brightening, comprising administering to a subject in need thereof a composition containing an effective amount of a *Chenopodium formosanum* (Djulis) extract obtained by extracting *Chenopodium formosanum* (Djulis) with water in a weight ratio of 1:10, and the extraction is performed at 85±5° C. for 60 minutes.

2. The method of claim 1, wherein the total flavonoid content of the *Chenopodium formosanum* (Djulis) extract is at least 1000 ppm.

3. The method of claim 1, wherein the total polyphenol content of the *Chenopodium formosanum* (Djulis) extract is at least 400 ppm.

4. The method of claim 1, wherein the effective amount of the *Chenopodium formosanum* (Djulis) extract is 0.5-2.0 mg/mL.

5. The method of claim 4, wherein the effective amount of the *Chenopodium formosanum* (Djulis) extract is 0.5-1.0 mg/mL.

6. The method of claim 1, wherein the effective amount of the *Chenopodium formosanum* (Djulis) extract is 10 wt %.

7. The method of claim 1, wherein the composition is a pharmaceutical composition, a health food composition, a food composition, or a cosmetic composition.

* * * * *

SEQUENCE LISTING

```
Sequence total quantity: 12
SEQ ID NO: 1            moltype = DNA  length = 21
FEATURE                 Location/Qualifiers
source                  1..21
                        mol_type = other DNA
                        organism = synthetic construct
SEQUENCE: 1
agagtggacc aactgaagag t                                              21

SEQ ID NO: 2            moltype = DNA  length = 21
FEATURE                 Location/Qualifiers
source                  1..21
                        mol_type = other DNA
                        organism = synthetic construct
SEQUENCE: 2
attctctgca tttgtccgct t                                              21

SEQ ID NO: 3            moltype = DNA  length = 22
FEATURE                 Location/Qualifiers
source                  1..22
                        mol_type = other DNA
                        organism = synthetic construct
SEQUENCE: 3
tcctacttgg acaaagttcg gg                                             22

SEQ ID NO: 4            moltype = DNA  length = 19
FEATURE                 Location/Qualifiers
source                  1..19
                        mol_type = other DNA
                        organism = synthetic construct
SEQUENCE: 4
cccctgatgt gagttgcca                                                 19

SEQ ID NO: 5            moltype = DNA  length = 22
FEATURE                 Location/Qualifiers
```

```
source                  1..22
                        mol_type = other DNA
                        organism = synthetic construct
SEQUENCE: 5
gatcgcatca cccttgagtt ac                                              22

SEQ ID NO: 6            moltype = DNA   length = 19
FEATURE                 Location/Qualifiers
source                  1..19
                        mol_type = other DNA
                        organism = synthetic construct
SEQUENCE: 6
gcaggttcag attctgccc                                                  19

SEQ ID NO: 7            moltype = DNA   length = 21
FEATURE                 Location/Qualifiers
source                  1..21
                        mol_type = other DNA
                        organism = synthetic construct
SEQUENCE: 7
agagtggacc aactgaagag t                                               21

SEQ ID NO: 8            moltype = DNA   length = 21
FEATURE                 Location/Qualifiers
source                  1..21
                        mol_type = other DNA
                        organism = synthetic construct
SEQUENCE: 8
attctctgca tttgtccgct t                                               21

SEQ ID NO: 9            moltype = DNA   length = 22
FEATURE                 Location/Qualifiers
source                  1..22
                        mol_type = other DNA
                        organism = Synthetic construct
SEQUENCE: 9
tcctacttgg acaaagttcg gg                                              22

SEQ ID NO: 10           moltype = DNA   length = 19
FEATURE                 Location/Qualifiers
source                  1..19
                        mol_type = other DNA
                        organism = synthetic construct
SEQUENCE: 10
cccctgatgt gagttgcca                                                  19

SEQ ID NO: 11           moltype = DNA   length = 20
FEATURE                 Location/Qualifiers
source                  1..20
                        mol_type = other DNA
                        organism = synthetic construct
SEQUENCE: 11
tataatccca agcggtttgc                                                 20

SEQ ID NO: 12           moltype = DNA   length = 20
FEATURE                 Location/Qualifiers
source                  1..20
                        mol_type = other DNA
                        organism = synthetic construct
SEQUENCE: 12
gctggaaaac ccaacttctg                                                 20
```